United States Patent
Louwsma et al.

(10) Patent No.: US 11,648,366 B2
(45) Date of Patent: May 16, 2023

(54) HUMIDIFIER FOR A SYSTEM FOR PROVIDING A FLOW OF BREATHABLE GAS

(71) Applicant: KONINKLIJKE PHILIPS N.V., Eindhoven (NL)

(72) Inventors: Hendrik Klaas Louwsma, Drachten (NL); Theodoor Stolk, Drachten (NL)

(73) Assignee: Koninklijke Philips N.V., Eindhoven (NL)

( * ) Notice: Subject to any disclaimer, the term of this patent is extended or adjusted under 35 U.S.C. 154(b) by 197 days.

(21) Appl. No.: 16/981,301

(22) PCT Filed: Jun. 24, 2019

(86) PCT No.: PCT/EP2019/066617
§ 371 (c)(1),
(2) Date: Sep. 16, 2020

(87) PCT Pub. No.: WO2020/002199
PCT Pub. Date: Jan. 2, 2020

(65) Prior Publication Data
US 2021/0113802 A1    Apr. 22, 2021

(30) Foreign Application Priority Data
Jun. 29, 2018   (EP) ..................................... 18180712

(51) Int. Cl.
*A61M 16/10*    (2006.01)
*A61M 16/16*    (2006.01)
*A61M 16/00*    (2006.01)

(52) U.S. Cl.
CPC ...... *A61M 16/1095* (2014.02); *A61M 16/109* (2014.02); *A61M 16/16* (2013.01);
(Continued)

(58) Field of Classification Search
CPC ..................... A61M 16/164; A61M 16/1045
See application file for complete search history.

(56) References Cited

U.S. PATENT DOCUMENTS 3,855,795 A * 12/1974 Noble ..................... F02G 1/043
                                                               60/524
5,231,979 A    8/1993 Dolida et al.
(Continued)

FOREIGN PATENT DOCUMENTS

JP    S49002357 A    1/1974
JP    S52002969 U    1/1977

OTHER PUBLICATIONS

International Search Report for PCT/EP2019/066617 dated Jun. 24, 2019.

*Primary Examiner* — Samchuan C Yao
*Assistant Examiner* — Tina Zhang
(74) *Attorney, Agent, or Firm* — Daniel H. Brean

(57) ABSTRACT

The present invention relates to a humidifier (10) for a system for providing a flow of breathable gas to an airway of a patient, wherein the humidifier (10) comprises: a casing (12) configured to contain a liquid reservoir (20); an air inlet (14) which is arranged at the casing (12); an air outlet (16) which is arranged at the casing (12); and a flow passage (18) connecting the air inlet (14) with the air outlet (16), wherein the flow passage (18) is in fluidic communication with the liquid reservoir (20), and wherein the humidifier (10) comprises a heat pipe (24) having a hot end (26) and a cold end (28), wherein the hot end (26) of the heat pipe (24) is arranged outside the casing (12) and the cold end (28) of the heat pipe (24) is arranged in the liquid reservoir (20).

15 Claims, 3 Drawing Sheets

(52) U.S. Cl.
CPC ... *A61M 16/0066* (2013.01); *A61M 2205/362* (2013.01); *A61M 2205/366* (2013.01); *A61M 2205/3606* (2013.01)

(56) References Cited

U.S. PATENT DOCUMENTS

| | | | |
|---|---|---|---|
| 5,598,837 A | | 2/1997 | Sirianne et al. |
| 5,916,493 A | * | 6/1999 | Miller ................. A61M 16/16 261/154 |
| 6,135,432 A | | 10/2000 | Brydon et al. |
| 8,662,479 B2 | | 3/2014 | Nichols et al. |
| 9,750,917 B2 | | 9/2017 | Seakins et al. |
| 2002/0020930 A1 | | 2/2002 | Austin et al. |
| 2009/0038614 A1 | | 2/2009 | Brieger et al. |
| 2009/0071479 A1 | * | 3/2009 | Nguyen ............. A61M 16/204 128/204.17 |
| 2010/0242961 A1 | | 9/2010 | Mocellin et al. |
| 2016/0361513 A1 | * | 12/2016 | Wang ..................... G06F 1/181 |
| 2017/0119992 A1 | | 1/2017 | Cho et al. |
| 2019/0134343 A1 | * | 5/2019 | Letton ................ A61M 16/021 |

\* cited by examiner

HUMIDIFIER FOR A SYSTEM FOR PROVIDING A FLOW OF BREATHABLE GAS

CROSS-REFERENCE TO PRIOR APPLICATIONS

This application claims the priority benefit under 35 U.S.C. § 371 of International Patent Application No. PCT/EP2019/066617, filed on Jun. 24, 2019, which claims the priority benefit of European Patent Application No. 18180712.4, filed on Jun. 29, 2018, the contents of which are hereby incorporated by reference.

FIELD OF THE INVENTION

The present invention relates to a humidifier for a system for providing a flow of breathable gas to an airway of a patient. The present invention further relates to the system comprising such a humidifier.

BACKGROUND OF THE INVENTION

Systems for providing a flow of breathable gas to an airway of a patient are applicable for the treatment and the therapy of several diseases and chronic dysfunctions where a patient needs, e.g. depending on the time of the day, supportive ventilation air or demands for a permanent ventilation. In such systems, gases like air, cleaned air, pure oxygen, or any modification thereof are delivered to the patient via a patient interface in a pressurized or unpressurized way.

Depending on the type of respiratory disease, the patient either needs to be actively ventilated by a so-called ventilator or ventilation system that takes over the breathing function of the patient, or the patient's breathing function needs to be merely supported by a pressurized flow of breathable gas. The present invention is directed to both of the aforementioned cases.

Ventilators which actively ventilate the patient are often used in hospitals. However, more and more ventilator devices are also implemented and targeted for the home use for treating several chronic respiratory diseases.

An example of a respiratory disease that does not afford an active ventilation of the patient but merely a breathing support is obstructive sleep apnea or obstructive sleep apnea syndrome (OSA). OSA is usually caused by an obstruction of the upper airway. It is characterized by repetitive pauses in breathing during sleep and is usually associated with a reduction in blood oxygen saturation. These pauses in breathing, called apneas, typically last 20 to 40 seconds. The obstruction of the upper airway is usually caused by reduced muscle tonus of the body that occurs during sleep. The human airway is composed of walls of soft tissue which can collapse and thereby obstruct breathing during sleep. In reaction to that, the tongue tissue moves towards the back of the throat during sleep and thereby blocks the air passages. OSA is therefore commonly accompanied with snoring.

Different invasive and non-invasive treatments for OSA are known. One of the most powerful non-invasive treatments is the usage of Continuous Positive Airway Pressure (CPAP) or Bi-Positive Airway Pressure (BiPAP) in which a patient interface, e.g. a face mask, is attached to a hose assembly and a machine (i.e. a pressure generator) that blows pressurized gas, preferably air, into the patient interface and through the airway of the patient in order to keep it open.

To minimize the possibility of dehydration, ventilation systems for permanent ventilation as well as CPAP and BIPAP systems preferably comprise a humidifier for humidifying air before delivering it to a patient's airway. For non-portable appliances, humidifiers often use a heating unit (i.e. a hot plate) to enhance evaporation of water and thus humidification of breathable air. The drawback of such a heating unit is usually its size and the necessity of connecting the heating unit to a power supply, which makes the system less handy and mobile. However, especially patients with a permanent ventilation requirement demand for smaller and lighter appliances that may be preferably portable to support their daily activities and thus to make confinement through their disease more tolerable, not only in home situations.

State of the art humidifiers for respiratory therapy devices can be categorized as passover or non-passover type humidifiers. Both types can be actively heated or not, wherein a non-heated passover humidifier is commonly known as a cold passover (CPO) humidifier. In a cold passover type humidifier without an additional heating unit, water is contained in a reservoir. While water is allowed to evaporate to produce vapor within the reservoir, breathable gas is passed over the water surface at a temperature of the ambient surrounding, or slightly above (i.e. due to heating effects of a pressure generator inside the therapy device). Due to evaporation, water cools down, and thus also cools down the overpassing therapy gas stream. This cooling takes place until an equilibrium is reached between the heat loss caused by evaporation and the heat intake into the system by the ambient surrounding, which can be between 12-14° C. when the system operates under normal room/ambient conditions and really dry air has to be humidified. If ambient temperature is higher (i.e. in regions next to the equator), a warmer water temperature results in the equilibrium state and thus warmer air exits the humidifier. Thus, fresh air leaving the humidifier is typically a few degrees colder than ambient temperature and the evaporation process is limited by the heat that the system can extract from the environment (typically 4-6 W for commercial CPO's). In a non-passover type humidifier, water is delivered into the gas stream via nebulization, atomization, vaporization, or a combination thereof.

An exemplary humidification system for a CPAP device for home-use or hospital-use is known from EP 2 219 720 B1.

An exemplary portable ventilator which comprises a humidifier is sold by the applicant under the name "Trilogy 100". However, such a system still demands for further improvements in terms of size, weight and humidification rate. Additionally, power consumption needs to be minimized in order to enable appliances to operate on a preferably small battery pack and thus to enable a flexible use with maximum comfort.

In order to fulfill these requirements, especially heating of humidifiers to increase humidification rate is a challenging aspect as such heated systems demand for both, a heating unit and a power supply (i.e. a battery) and thus contradict ostensibly with reduction of size and weight.

SUMMARY OF THE INVENTION

It is an objective of the present invention to provide a humidifier for a system for providing a flow of breathable gas to an airway of a patient that overcomes the shortcomings of conventional humidification systems.

In a first aspect of the present invention, a humidifier for a system for providing a flow of breathable gas to an airway of a patient is presented, wherein the humidifier comprises: a casing configured to contain a liquid reservoir;
an air inlet which is arranged at the casing;
an air outlet which is arranged at the casing; and
a flow passage connecting the air inlet with the air outlet, wherein the flow passage is in fluidic communication with the liquid reservoir, and wherein the humidifier comprises a heat pipe having a hot end and a cold end, wherein the hot end of the heat pipe is arranged outside the casing and the cold end of the heat pipe is arranged in the liquid reservoir.

In a further aspect of the present invention, a system for providing a flow of breathable gas to an airway of the patient is presented, comprising the aforementioned humidifier.

The usage of a heat pipe in the presented humidifier enables an easily portable system without the need of a connection to an external power supply. Since the hot end of the heat pipe may, depending on the application and ambient condition, be arranged at almost any selected (preferably warm) place, the present invention further enables a large freedom of design to capture heat from the environment in a most suitable way.

In the presented humidifier, the amount of heat extracted from the environment through the heat pipe heats up the liquid in the liquid reservoir and thus maintains evaporation on a high rate without using an external power supply. The heat pipe preferably provides a heating power of 5-15 W. The liquid of the liquid reservoir is preferably water. Thus, the equilibrium of the evaporation process is reached at a higher water temperature, where more liquid can be evaporated. As a consequence, the flow of the breathable gas, preferably air, passing through the flow passage and exiting the humidifier at the air outlet can accumulate more liquid and is cooled down less, exiting the humidifier a few degrees higher compared to a case without additional heating by the heat pipe.

Depending on the specific application, the casing which is configured to contain the liquid reservoir, can differ in size and shape and may be made of a preferably transparent or non-transparent plastic, metal or any other feasible material. It is preferable that the casing comprises a sealable opening to refill the liquid reservoir, to guarantee a certain filling level somewhere between a minimum and a maximum filling level.

The air inlet and the air outlet can be located or arranged at the casing in any suitable position (i.e. at the side walls or the cover plate), wherein it is preferable that their location is arranged in such a manner that no liquid from the liquid reservoir can flow inside or enter the air inlet or the air outlet.

The flow passage is preferably arranged inside the casing of the humidifier between the air inlet and the air outlet. The flow passage is preferably surrounded by the walls of the casing.

The term "fluidic communication" means that the liquid reservoir is configured to lead the flow of breathable gas over a surface of the liquid reservoir, or the liquid reservoir is configured to ensure in any other way that the flow of breathable gas is allowed to come into contact with the evaporated liquid from the liquid reservoir.

The cold end of the heat pipe is arranged inside the liquid reservoir (preferably fully surrounded by the liquid) and is configured to transfer heat to the surrounding liquid.

The hot end of the heat pipe is arranged outside the casing of the humidifier so as to get heated e.g. by the ambient air in the external environment. Heat is therefore transferred inside the heat pipe from the hot end to the cold end, and, at the cold end, heat is transferred from the heat pipe to the liquid that is to be evaporated and stored in the liquid reservoir.

According to embodiment of the invention, the hot end of the heat pipe is arranged distanced from the casing of the humidifier.

An advantage of such an embodiment is that a distanced arrangement of the hot end of the heat pipe from the cold end gives freedom to design and enables the possibility to capture heat (i.e. from the environment) in another location distanced from the actual arrangement of the humidifier. For example, it may be possible to install the hot end of the heat pipe in the vicinity of one of the side walls of the casing instead of the bottom of the casing to keep the bottom surface available for additional energy scavenging (i.e. caused by direct heat transfer through the wall/bottom of the casing). In other words, this embodiment makes it possible "to collect" heat anywhere, where large exposure of heat to the ambiance takes place. Being arranged "distanced from the casing of the humidifier" means in this case "not in direct contact with the casing of the humidifier".

According to another embodiment of the invention, a heat exchanger is arranged at the hot end of the heat pipe.

An advantage of this embodiment is that an overall efficient heat transport through the internals and externals of the heat pipe can be further enhanced by the placement of an additional heat exchanger at the end of the heat pipe which is arranged outside of the humidifier. Hereby, the external parts of the heat pipe consist of heat conducting material, e.g. metal, to quickly pick up and release the heat. Therefore, also the externals of the heat pipe act as a conductor between cold end and the hot end of the heat pipe. Such a heat exchanger is in direct thermal contact with the surface of the heat pipe (most favorably in such a manner that heat losses at the boundary surface can be minimized). With such a heat exchanger, it is possible to maximize the surface area for collecting heat from the environment which leads to enhanced performance.

According to another embodiment of the invention, the heat exchanger comprises a cooling fin.

While arranging only one cooling fin is possible, it is favorable to arrange a plurality of cooling fins at the hot end of the heat pipe. Such cooling fins function as heat exchangers which maximize the surface area for collecting heat. The cooling fin(s) is/are preferably in direct thermal contact with the heat pipe.

The location of the cooling fin and the heat exchanger at the end of the heat pipe can be chosen conveniently, for example at the back of the humidifier instead of the bottom. Instead of cooling fins, it is possible to use other geometries with a different shape and size increasing the overall surface for heat collection.

In another embodiment of the invention, the heat pipe contains a fluid pressurized at a first pressure, wherein the fluid is configured to evaporate at an evaporation temperature of 10 to 40° C. at the first pressure.

The pressurized fluid inside the heat pipe is considered to evaporate at the hot end of the heat pipe at the evaporation temperature. The vaporized fluid flows, driven by the temperature difference between the hot end and the cold end of the heat pipe, to the cold end of the heat pipe, where condensation takes place. During condensation of the vaporized fluid, heat is transferred through the surrounding walls of the heat pipe into the surrounding liquid. The condensed fluid flows back, preferably partly driven by capillary force, favorably supported by gravity, to the hot end of the heat pipe, where the fluid evaporates again due to the heat supplied by the environment surrounding at the hot end of the heat pipe.

In another embodiment of the invention, the heat pipe is of a substantially tubular shape.

Such a shape is favorable for a homogenous heat flux over the surface of the heat pipe.

In another embodiment of the invention, parts of the hot end and/or parts of the cold end of the heat pipe are of a substantially plate-like shape.

An advantage of this embodiment is that the surface contact area with the liquid and/or the environment at the hot end and/or the cold end of the heat pipe can be maximized, respectively. Thereby, the rate of heat exchange can be increased. Furthermore, it is possible to extend the hot end and/or the cold end of the heat pipe in order to further maximize the surface area for conduction.

In another embodiment of the invention, the hot end of the heat pipe is positioned below the cold end of the heat pipe.

An advantage of this embodiment is that the reflux of the condensed fluid inside the heat pipe can be supported by gravity, as the hot end of the heat pipe is positioned below the cold end of the heat pipe.

In another embodiment of the invention, the longitudinal cross-section of the heat pipe is substantially U-shaped.

Such a U-shaped heat pipe is space-saving and still provides the above-mentioned advantages. However, other shapes and geometries of the heat pipe may also be favorable according to the particular application.

In another embodiment of the invention, the system for providing a flow of breathable gas to an airway of the patient comprises the presented humidifier, a pressure generator, a patient interface, and a hose assembly connecting the pressure generator to the patient interface.

The system is configured to deliver pressurized air coming from the pressure generator to the patient interface through the hose assembly connecting the pressure generator to the patient interface. The presented humidifier may generally be placed upstream or downstream the pressure generator. The presented humidifier is favorably connected gastight with parts of the hose assembly to enable the flow of breathable, humidified gas to the airway of a patient. Hereby, the patient interface may be a mask covering the nose, mouth and/or face of the patient. The patient interface may however also be realized as a device that is inserted into the mouth and/or the nostrils of the patient or directly in the patients trachea.

In another embodiment of the invention, the system further comprises a housing which is configured to contain the pressure generator and the humidifier.

Such a housing may be a box or a case containing the pressure generator and the humidifier, wherein the design of the housing may preferably ensure that electric components (i.e. of the pressure generator) can be arranged separately from wet components (i.e. from the humidifier) inside the casing to prevent shortcuts and thereby enable a safe use for the patient. An advantage of such an embodiment is that the patient or user of the device only needs to transport a single housing which increases the comfort.

In another embodiment of the invention, the humidifier is arranged in a flow path between the pressure generator and the patient interface.

Thereby, the humidifier is connected gastight to the pressure generator and the patient interface via parts of the hose assembly to ensure the flow of breathable gas to the airway of the patient. It should be mentioned that it is possible to arrange the humidifier outside or separate from the pressure generator in two different housings or in the same housing, respectively.

In another embodiment of the invention, the system further comprises an exhaust air outlet, wherein the hot end of the heat pipe is arranged at or in the vicinity of the exhaust air outlet.

This location enables the possibility to "collect" a warm flow of exhaust air which increases the amount of deliverable heat to the liquid reservoir. It should be mentioned that the arrangement of the hot end of the heat pipe can be determined, according to the overall arrangement of the device, directly at the exhaust air outlet or distanced to that. Such an exhaust air outlet might be located at the housing of the device to ensure that hot exhaust air (i.e. coming from a motor of the pressure generator or from electronic devices) exits the housing and a predetermined temperature inside the housing is maintained.

In another embodiment of the invention, the system further comprises a fan or blower configured to direct a convective flow of exhaust air exiting the exhaust air outlet to the hot end of the heat pipe.

Such a configuration is not a pure passive system and will require some power to run the fan or blower. The required power could be delivered by a small battery which might be preferably rechargeable via an external electricity supply.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

Figure 1:
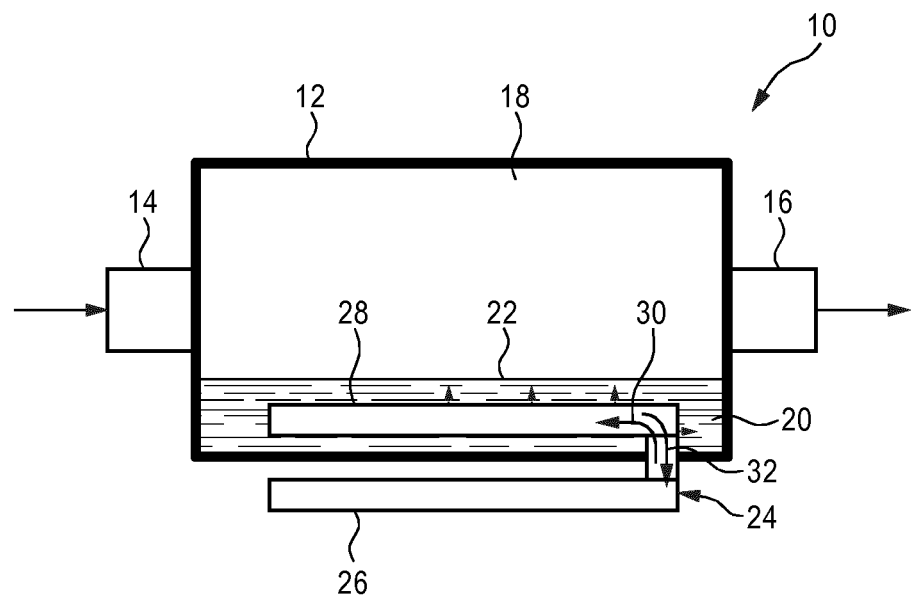
FIG. 1 shows a first embodiment of the humidifier according to the present invention.

FIG. 1 shows a first embodiment of the humidifier for a system for providing a flow of breathable gas to an airway of a patient. The humidifier is therein in its entirety denoted by reference numeral 10.

The humidifier 10 comprises a casing 12 with an air inlet 14 arranged at the left sidewall of the casing 12 and an air outlet 16 arranged at the right sidewall of the casing 12 (regarding a plane view perspective). The air inlet 14 and the air outlet 16 are connected via a flow passage 18, which is located inside the casing 12 and which is in fluidic communication with a liquid reservoir 20.

In FIG. 1, this fluidic communication mainly takes place at a boundary surface 22 between the flow passage 18 and the liquid reservoir 20 and thus, directly on or slightly above the surface 22 of the liquid reservoir 20.

The liquid reservoir 20 may e.g. contain water as a liquid. A flow of breathable gas, in this case air, may enter the humidifier 10 through the air inlet 14, accumulate evaporating water from the liquid reservoir 20, and leave the casing 12 through the air outlet 16 at a higher humidity level.

Due to evaporation, the liquid inside the liquid reservoir 20 cools down. In order to prevent a too severe temperature drop of the water, a heat pipe 24 having a hot end 26 and a cold end 28 is arranged at the humidifier 10 in such a manner that the cold end 28 of the heat pipe 24 is arranged inside the liquid reservoir 20 and the hot end 26 of the heat pipe 24 is arranged outside the casing 12.

In FIG. 1, the heat pipe 24 is of a substantially tubular shape and furthermore shows a U-shaped design, where the hot end 26 is located between the cold end 28 of the heat pipe 24. The hot end 26 of the heat pipe 24 is positioned below the cold end 28 of the heat pipe 24. Such a location of the hot end 26 enhances the reflux of the pressurized fluid inside the heat pipe 24 by gravity.

The heat pipe 24 contains a fluid pressurized at a first pressure p1, wherein the fluid evaporates at an evaporation temperature T1 at the hot end 26 of the heat pipe 24 and flows in the vaporized state along a first flow direction 30 to the cold end 28 of the heat pipe 24, where condensation of the pressurized fluid takes place. The condensing fluid passes its heat through the walls of the heat pipe 24 to the surrounding water of the liquid reservoir 20 and flows back along a second flow direction 32 where the pressurized fluid evaporates again.

The circulation of the pressurized fluid inside the heat pipe 24 is enabled as a certain amount of heat is collected from the surrounding of the hot end 26 of the heat pipe 24 in its location outside the casing 12.

Figure 2:
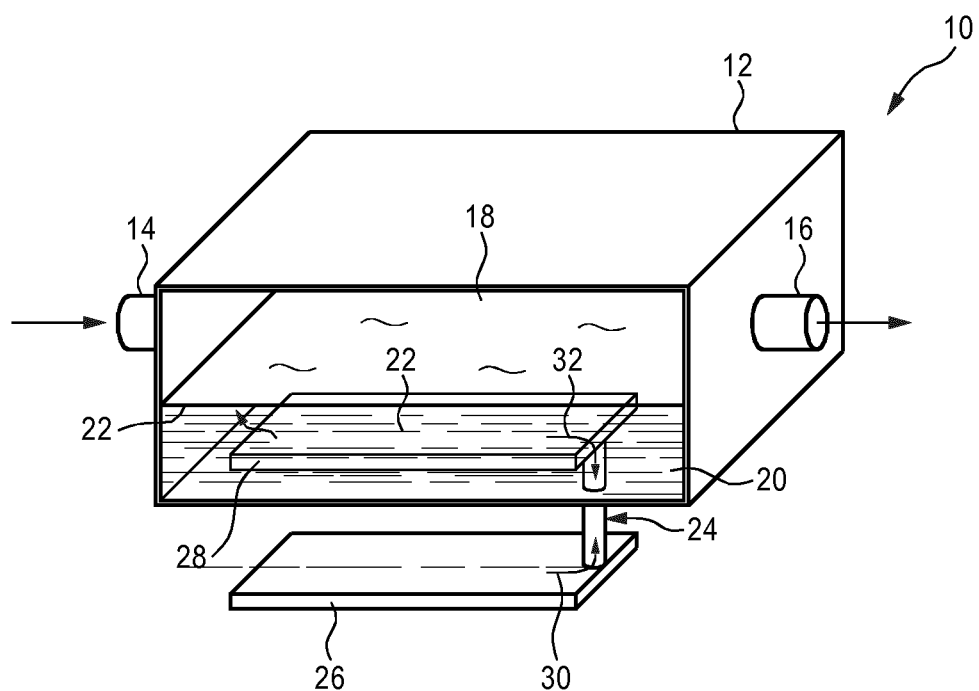
FIG. 2 shows a second embodiment of the humidifier according to the present invention.

In FIG. 2, the heat pipe 24 shows, different from the heat pipe 24 in FIG. 1, a plate-like, U-shaped design of the hot end 26 and the cold end 28. With such a shape, the surface area of the heat pipe 24 is increased, which increases the rate of heat transfer at the cold end 28 of the heat pipe 24 as well as at the hot end 26 of the heat pipe 24. The functionality of the humidifier 10 shown in FIG. 2 is similar to FIG. 1.

Figure 3:
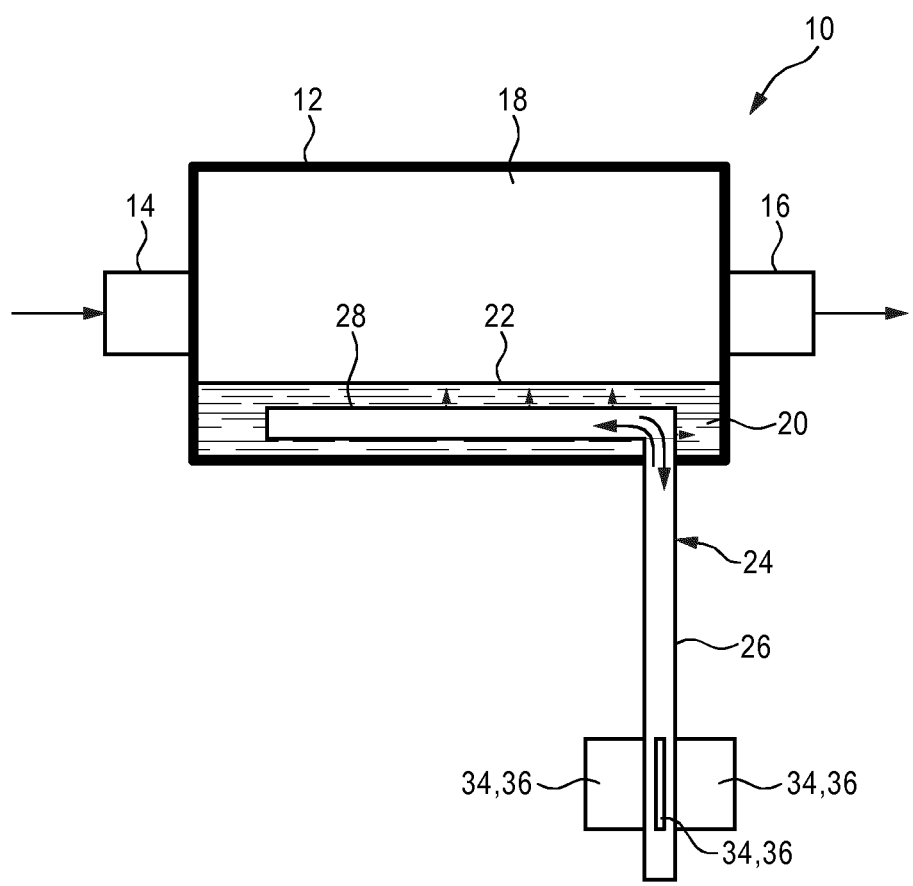
FIG. 3 shows a third embodiment of the humidifier according to the present invention.

FIG. 3 shows a third embodiment of the humidifier 10 according to the present invention. In this embodiment, the hot end 26 of the heat pipe 24 protrudes in a rectangular angle from the casing 12 of the humidifier 10, wherein the heat pipe 24 shows a substantially tubular shape. Additionally, at the end of the hot end 26 of the heat pipe 24 a heat exchanger 34 is arranged in form of fins 36, which are in thermal contact with the surface of the hot end 26 of the heat pipe 24. It is clear that the angle between the hot end 26 of the heat pipe 24 and the casing 12 does not necessarily have to be a right angle. It is however preferred that the hot end 26 protrudes from the casing 12 such that at least parts of the hot end 26 are arranged distanced from the casing 12 and are exposed to the ambient environment. The hot end 26 of the heat pipe 24 is positioned below the cold end 28 of the heat pipe 24.

Figure 4:
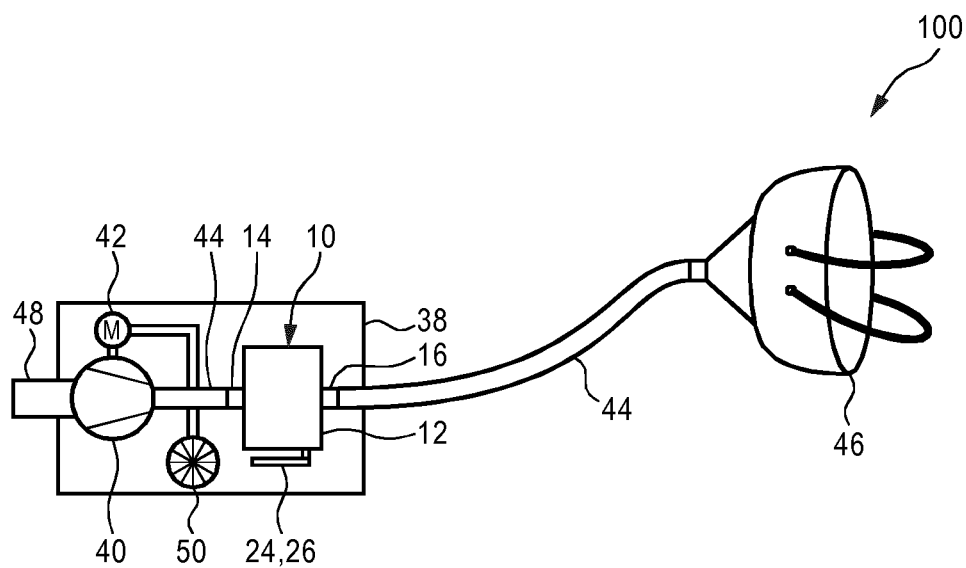
FIG. 4 shows a first embodiment of the system according to the present invention.

FIG. 4 shows a first embodiment of a system 100 for providing a flow of breathable gas to an airway of a patient, wherein the system 100 comprises a humidifier 10 according to the present invention.

In this embodiment, the humidifier 10 is located inside a housing 38 together with a pressure generator 40 which is driven by a motor 42. The pressure generator 40 is connected airtight to the air inlet 14 of the humidifier 10 via parts of a hose assembly 44. The air outlet 16 of the humidifier 10 is connected via parts of the hose assembly 44 with a patient interface 46, configured to deliver breathable gas to the airway of the patient via the nose and/or mouth.

The pressure generator 40 intakes breathable gas through an inlet 48 (i.e. from the surrounding) and pressurizes the intake gas via the driving force of the motor 24. The pressurized air flows through the humidifier accumulating water from the liquid reservoir 20.

The humidified flow of breathable gas exits the humidifier 10 through the air outlet 16 flowing through the hose assembly 44 into the patient interface 46 delivering the patient's airway with the flow of breathable, humidified gas.

In FIG. 4, the motor 42 for running the pressure generator 40 produces exhaust air with a higher temperature compared to the surrounding outside the housing 38, wherein the exhaust air exits the housing 38 through an exhaust air outlet 50. The exhaust air outlet 50 is, in this case, located at the bottom part of the back wall of the housing 38. The hot end 26 of the heat pipe 24 is exposed to the space inside the housing 38 outside the casing 12 of the humidifier 10. In this arrangement, the hot end 26 of the heat pipe 24 can collect heat from the exhaust air produced by the motor 42. Due to this hot exhaust air, heat intake at the hot end 26 of the heat pipe 24 is increased, which increases in turn the evaporation rate of the pressurized fluid inside the heat pipe 24 and thus the amount of heat which can be transferred through the walls of the heat pipe 24 to the surrounding liquid of the liquid reservoir 20.

Figure 5:
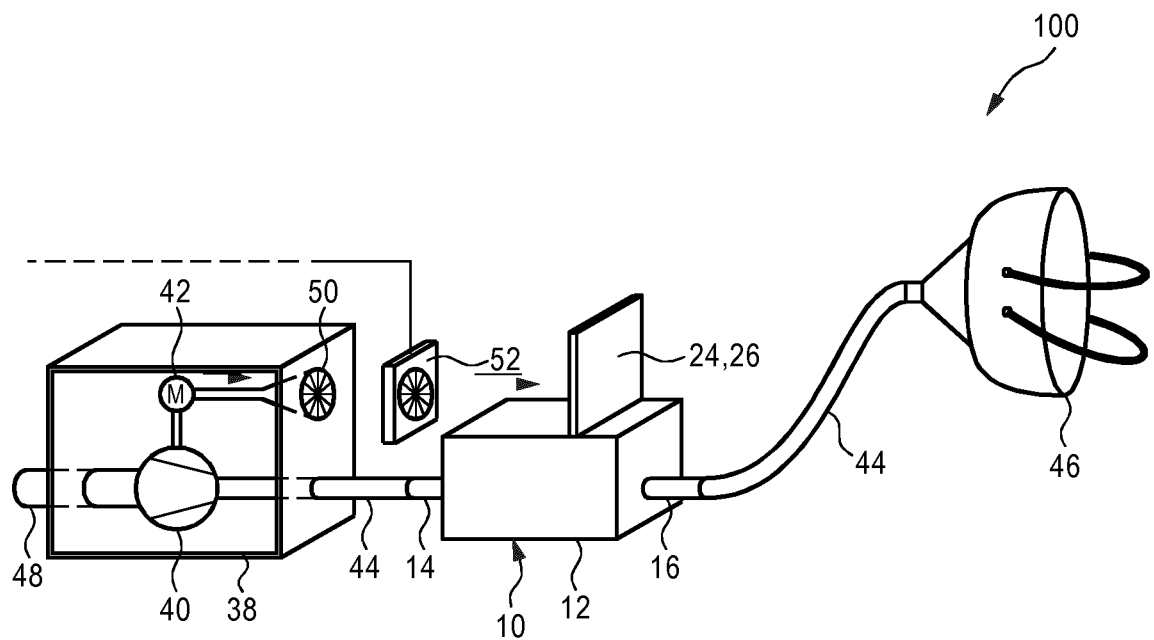
FIG. 5 shows a second embodiment of the system according to the present invention.

FIG. 5 shows an embodiment of the device 100, where the humidifier 10 is located outside the housing 38. The pressure generator 14 is connected to the humidifier 10 via parts of the hose assembly 44. In this embodiment, the hot end 26 of the heat pipe 24 is located on the upper side of the casing 12 of the humidifier 10 and shows a plate-like shape. In further embodiments, the hot end 26 of the heat pipe 24 could also be located below the casing 12, depending on the location of the exhaust air outlet 50 of the pressure generator 40 and the relative position of the humidifier 10 to the pressure generator 40. In this arrangement, a fan 52 is arranged in the flow direction of the exhaust air outlet 50 forcing the flow of exhaust air to penetrate the surface of the hot end 26 of the heat pipe 24 to increase the heat transfer to the liquid reservoir 20 inside the humidifier 10. It is clear that such a fan 52 could similarly be used in an arrangement as shown in FIG. 4, where the humidifier 10 is arranged together with the pressure generator 40 inside the housing 38. It should also be mentioned that the embodiment shown in FIG. 5 would also work without the additional fan 52, i.e. in case where the hot end 26 of the heat pipe 24 is located near the exhaust air outlet 50 of the pressure generator 40.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A humidifier for a system for providing a flow of breathable gas to an airway of a patient, wherein the humidifier comprises:

a casing configured to contain a liquid reservoir;

an air inlet which is arranged at the casing;
an air outlet which is arranged at the casing; and
a flow passage connecting the air inlet with the air outlet, wherein the flow passage is in fluidic communication with the liquid reservoir;
a heat pipe having a first end and a second end, wherein the first end of the heat pipe is arranged outside the casing and configured to be heated by an ambient environment relative to the humidifier and the second end of the heat pipe is arranged in the liquid reservoir.

2. The humidifier according to claim 1, wherein the first end of the heat pipe is arranged distanced from an exterior of the casing of the humidifier.

3. The humidifier according to claim 1, wherein a heat exchanger is arranged at the first end of the heat pipe.

4. The humidifier according to claim 3, wherein the heat exchanger comprises a cooling fin.

5. The humidifier according to claim 1, wherein the heat pipe contains a fluid pressurized at a first pressure, wherein the fluid is configured to evaporate at an evaporation temperature of 10 to 40° C. at the first pressure.

6. The humidifier according to claim 1, wherein the heat pipe is of a substantially tubular shape.

7. The humidifier according to claim 1, wherein parts of the first end and/or parts of the second end of the heat pipe are of a substantially U-shape.

8. The humidifier according to claim 1, wherein the first end of the heat pipe is positioned below the second end of the heat pipe.

9. The humidifier according to claim 1, wherein a cross-section of the heat pipe is substantially U-shaped.

10. A system for providing a flow of breathable gas to an airway of a patient, comprising a humidifier according to claim 1.

11. The system according to claim 10, further comprising:
a pressure generator;
a patient interface; and
a hose assembly connecting the pressure generator to the patient interface.

12. The system according to claim 11, further comprising a housing which is configured to contain the pressure generator and the humidifier.

13. The system according to claim 11, wherein the humidifier is arranged in a flow path between the pressure generator and the patient interface.

14. The system according to claim 10, further comprising an exhaust air outlet, wherein the first end of the heat pipe is arranged at or in the vicinity of the exhaust air outlet.

15. The system according to claim 14, further comprising a fan or blower configured to direct a convective flow of exhaust air exiting the exhaust air outlet to the first end of the heat pipe.

* * * * *